(12) United States Patent
Dell'Oca

(10) Patent No.: US 9,603,565 B2
(45) Date of Patent: Mar. 28, 2017

(54) SINGLE PATIENT USE DEPTH GAUGE

(71) Applicant: SYNTHES USA, LLC, West Chester, PA (US)

(72) Inventor: Alberto Fernandez Dell'Oca, Montevideo (UY)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 117 days.

(21) Appl. No.: 13/727,906

(22) Filed: Dec. 27, 2012

(65) Prior Publication Data
US 2014/0012159 A1 Jan. 9, 2014

Related U.S. Application Data

(60) Provisional application No. 61/582,025, filed on Dec. 30, 2011, provisional application No. 61/598,922, filed on Feb. 15, 2012.

(51) Int. Cl.
*A61B 5/107* (2006.01)
*A61B 5/00* (2006.01)
(Continued)

(52) U.S. Cl.
CPC .......... *A61B 5/4504* (2013.01); *A61B 5/1072* (2013.01); *A61B 90/06* (2016.02);
(Continued)

(58) Field of Classification Search
CPC . A61B 5/4504; A61B 19/46; A61B 2019/462; A61B 2017/0023; A61F 2/4657; A61F 2002/4662

USPC .......... 600/587; 606/102; 33/512, 515, 836; 73/431, 432.1, 866.5; 254/120, 129, 131; 81/489, 491, 487, 488; 433/72, 74–76
See application file for complete search history.

(56) References Cited

U.S. PATENT DOCUMENTS 517,073 A * 3/1894 Sloane ............................ 33/831
1,327,114 A * 1/1920 Rhein ............................ 33/514
(Continued)

FOREIGN PATENT DOCUMENTS

CN 101166465 4/2008
CN 101677784 3/2010
(Continued)

*Primary Examiner* — Devin Henson
*Assistant Examiner* — David J McCrosky
(74) *Attorney, Agent, or Firm* — Fay Kaplun & Marcin, LLP

(57) ABSTRACT

A device for guiding a depth gauge for measuring blind holes formed through a bone including (a) a handle having an elongated body, an upper surface of the body having a peg extending therefrom to removably engage a proximal end of a first elongated rod of the depth gauge, the handle including a first slot extending into the upper surface and open to a first elongated channel extending through the handle and (b) a first elongated shaft extending through the first elongated channel and including a first tab extending through the first slot, a range of movement of the first elongated shaft relative to the handle being limited by engagement of the first tab with walls of the first slot. In an operative configuration, the slotted tab receives a proximal end of the depth gauge to control movement of an increased diameter insert at a distal end thereof.

21 Claims, 4 Drawing Sheets

(51) Int. Cl.
*A61F 2/46* (2006.01)
*G01B 3/28* (2006.01)
*A61B 90/00* (2016.01)
*A61B 17/00* (2006.01)

(52) U.S. Cl.
CPC .............. *A61F 2/4657* (2013.01); *G01B 3/28* (2013.01); *A61B 2017/0023* (2013.01); *A61B 2090/061* (2016.02); *A61B 2090/062* (2016.02); *A61F 2002/4662* (2013.01)

(56) References Cited

U.S. PATENT DOCUMENTS

| | | | |
|---|---|---|---|
| 3,964,170 A * | 6/1976 | Zdarsky | 33/513 |
| 4,033,043 A * | 7/1977 | Cunningham | 33/806 |
| 4,238,885 A | 12/1980 | Lendi et al. | |
| 4,312,363 A | 1/1982 | Rothfuss et al. | |
| 5,409,493 A * | 4/1995 | Greenberg | 606/96 |
| 5,620,449 A | 4/1997 | Faccioli et al. | |
| 6,295,671 B1 | 10/2001 | Reesby et al. | |
| 7,101,181 B2 * | 9/2006 | Bompard et al. | 433/75 |
| 7,134,216 B2 | 11/2006 | Rupp et al. | |
| 7,293,364 B2 * | 11/2007 | Dace et al. | 33/512 |
| 7,559,150 B2 | 7/2009 | Fernandez | |
| 7,823,296 B2 | 11/2010 | Dell'Oca | |
| 7,976,550 B2 * | 7/2011 | Trudeau | 606/99 |
| 2002/0104230 A1 | 8/2002 | White | |
| 2005/0066535 A1 | 3/2005 | Rupp et al. | |
| 2006/0207118 A1 | 9/2006 | Kim | |
| 2006/0207119 A1 * | 9/2006 | Kim et al. | 33/512 |
| 2006/0224161 A1 | 10/2006 | Bhattacharyya | |
| 2007/0088366 A1 | 4/2007 | Fernandez | |
| 2007/0227023 A1 | 10/2007 | Dace et al. | |
| 2008/0039860 A1 | 2/2008 | Trudeau | |
| 2009/0005786 A1 | 1/2009 | Prien et al. | |
| 2009/0157088 A1 | 6/2009 | Mengato | |
| 2009/0272001 A1 | 11/2009 | Dell'Oca | |
| 2009/0326533 A1 | 12/2009 | Dell'Oca | |
| 2010/0154238 A1 | 6/2010 | Harshbarger et al. | |
| 2010/0228350 A1 | 9/2010 | Gornet et al. | |
| 2012/0191104 A1 | 7/2012 | Jost et al. | |

FOREIGN PATENT DOCUMENTS

| | | |
|---|---|---|
| CN | 201578245 | 9/2010 |
| CN | 101874737 | 11/2010 |
| CN | 201879693 | 6/2011 |
| CN | 201920730 | 8/2011 |
| DE | 20011156 | 12/2000 |
| EP | 1 938 039 | 7/2008 |
| JP | S55-3000 | 1/1980 |
| JP | S56-121537 | 9/1981 |
| WO | 2007/047466 | 4/2007 |

\* cited by examiner

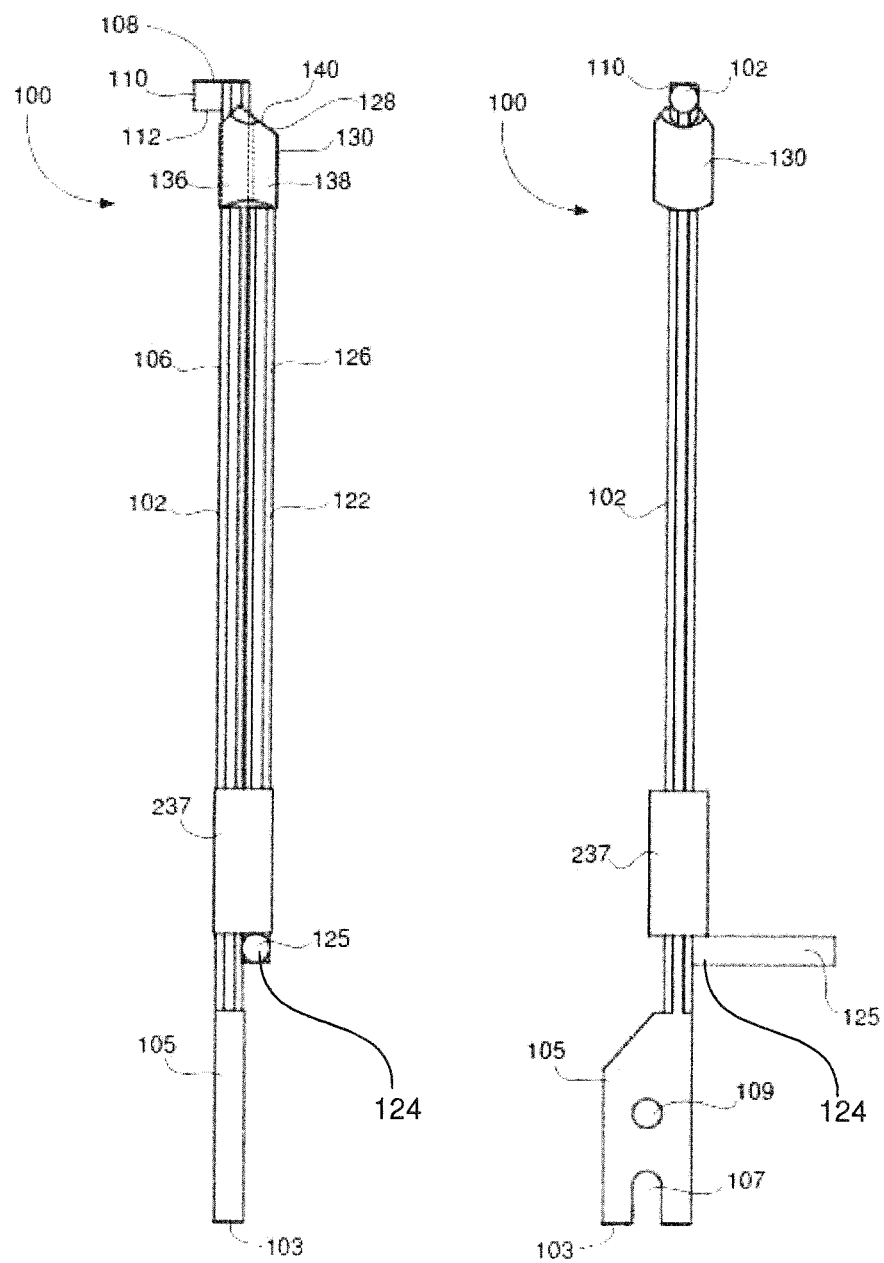

they will be used with the measurement of holes drilled through a bone in accordance with a bone fixation procedure for a fractured or otherwise damaged bone. The depth gauge according to the invention includes first and second elongated, substantially cylindrical rods. The first rod includes an elongated shaft and an abutment at a distal end thereof with a diameter greater than that of a portion of the shaft extending proximally therefrom. The diameter of the abutment is smaller than the diameter of the blind hole to permit insertion of the abutment therethrough. The second rod includes an elongated shaft having an increased diameter insert at a distal end thereof. The insert includes an opening extending therethrough to slidably receive the shaft of the first rod. In an operative configuration, the first rod is slidably received within the opening of the second rod. Manipulation of the individual components of the depth gauge is carried out by an exemplary handle according to the invention, which comprises first and second individually movable levers. The first lever is connected to a housing slidably receiving the first and second rods therethrough, the housing operably indicating a depth of insertion of the depth gauge probe, as will be described in greater detail later on. The handle includes an engagement mechanism (i.e., a peg) removably engaging an increased diameter portion provided on a proximal end of the first rod so that movement of the handle results in a corresponding movement of the first rod. The second lever is operably connected to the second rod to control proximal and distal movement thereof.

SINGLE PATIENT USE DEPTH GAUGE

PRIORITY CLAIM

The present application claims priority to U.S. Provisional Appln. Ser. No. 61/598,922 entitled "Single Patient Use Depth Gauge" filed on Feb. 15, 2012 and U.S. Provisional Appln. Ser. No. 61/582,025 entitled "Round Depth Gauge" filed on Dec. 30, 2011, the entire disclosures of which are incorporated herein by reference.

BACKGROUND

Bone fixation procedures often require the insertion of a bone screw transversely though a bone. In such cases, it is necessary to assess the depth of a hole formed through the bone. Existing measurement devices include a calibrated rod having a single hook provided on an end thereof. In operation, the rod is inserted through the bone hole and, after emerging from a opposing end of the bone hole, the rod is retracted until it abuts against a blind edge adjacent the opposing end. The disadvantage of such devices is that hooking the edge of the bone hole is quite difficult, especially when measuring smaller diameter holes. There is a need for a hole-depth measuring instrument that provides a fast and accurate measurement. There is a further need for a measuring instrument which firmly engages the opposing distal edge of the bone hole to allow for a precise measurement of the bone hole.

SUMMARY OF THE INVENTION

The present invention is directed to a device for guiding a depth gauge for measuring blind holes formed through a bone, comprising a handle having an elongated body, an upper surface of the body having a peg extending therefrom to removably engage a proximal end of a first elongated rod of the depth gauge, the handle including a first slot extending into the upper surface and open to a first elongated channel extending through the handle in combination with a first elongated shaft extending through the first elongated channel and including a first tab extending through the first slot, a range of movement of the first elongated shaft relative to the handle being limited by engagement of the first tab with walls of the first slot wherein, in an operative configuration the slotted tab receives a proximal end of the depth gauge to control movement of an increased diameter insert at a distal end thereof.

BRIEF DESCRIPTION OF THE DRAWINGS

FIG. 5 shows a side view of a depth gauge for use with the handle of FIG. 1; and FIG. 6 shows a top view of the depth gauge of FIG. 5.

DETAILED DESCRIPTION

Figure 1:
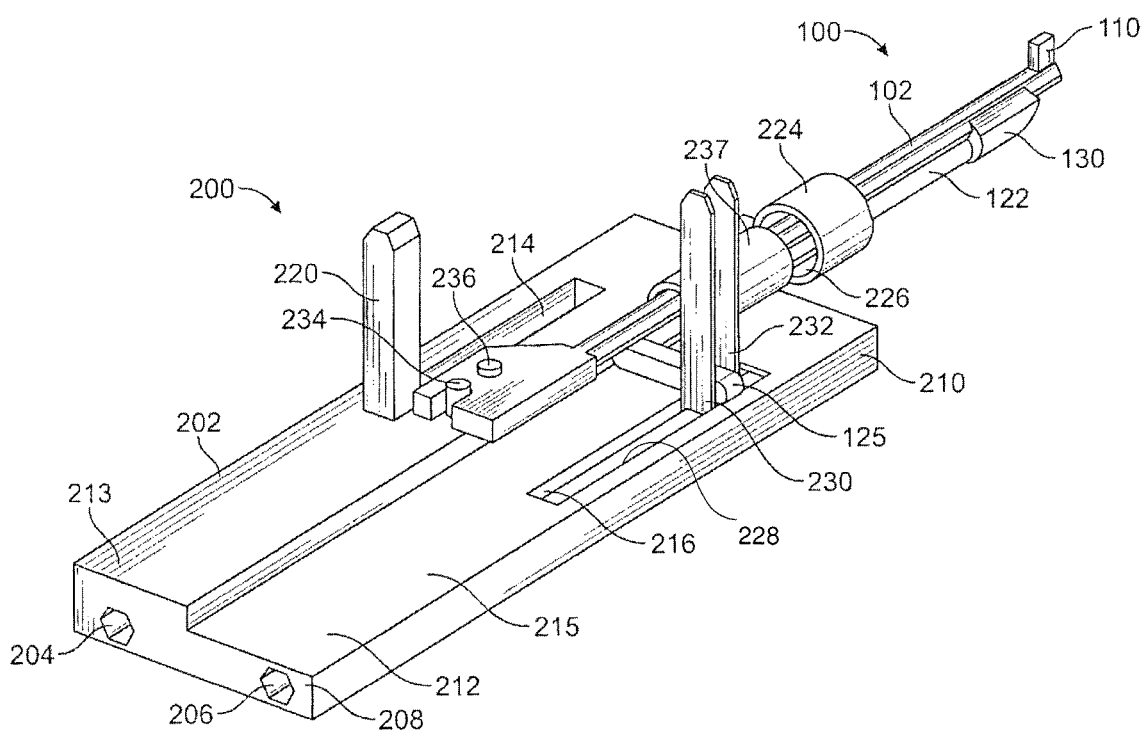
FIG. 1 shows a first perspective view of a depth gauge handle according to an exemplary embodiment of the invention.

The present invention may be further understood with reference to the following description and the appended drawings, wherein like elements are referred to with the same reference numerals. The present invention relates to an exemplary handle for used with an exemplary depth gauge to be used for the measurement of holes drilled through a bone in accordance with a bone fixation procedure for a fractured or otherwise damaged bone. The depth gauge according to the invention includes first and second elongated, substantially cylindrical rods. The first rod includes an elongated shaft and an abutment at a distal end thereof with a diameter greater than that of a portion of the shaft extending proximally therefrom. The diameter of the abutment is smaller than the diameter of the blind hole to permit insertion of the abutment therethrough. The second rod includes an elongated shaft having an increased diameter insert at a distal end thereof. The insert includes an opening extending therethrough to slidably receive the shaft of the first rod. In an operative configuration, the first rod is slidably received within the opening of the second rod. Manipulation of the individual components of the depth gauge is carried out by an exemplary handle according to the invention, which comprises first and second individually movable levers. The first lever is connected to a housing slidably receiving the first and second rods therethrough, the housing operably indicating a depth of insertion of the depth gauge probe, as will be described in greater detail later on. The handle includes an engagement mechanism (i.e., a peg) removably engaging an increased diameter portion provided on a proximal end of the first rod so that movement of the handle results in a corresponding movement of the first rod. The second lever is operably connected to the second rod to control proximal and distal movement thereof.

In an operative configuration, the single-use depth gauge is attached to the reusable handle, which guides positioned of the depth gauge against a proximal opening of the bone hole. The handle is then advanced distally to cause a corresponding distal movement of the first rod such that the abutment passes through the bone hole and out of a distal side of the bone. Once the abutment has moved distally through the distal opening of the hole, the second lever is advanced distally to cause a corresponding distal movement of the second rod relative to the first rod through the bone out the distal opening of the hole until engagement of the insert with the abutment prevents further distal movement thereof. In this configuration, the abutment projects radially outward beyond the edge of the blind hole so that the abutment is physically prevented from being withdrawn into the blind hole. Thus, only the insert having the first rod received therethrough, which has a combined diameter closely matching a diameter of the bone hole is capable of being drawn into the bone hole. The first and second rods are then moved proximally via the handle until the abutment is seated against a portion of the bone adjacent the distal opening. The first lever is then advanced distally to guide the substantially cylindrical housing provided over proximal portions of the first and second rods to move distally until a distal end of the housing is seated against a proximal opening of the hole. In this configuration, markings provided on the second rod indicate the depth of insertion of the depth gauge into the bone and, consequently, a length of the hole formed in the bone. The exemplary depth gauge and handle according to the invention permit the abutment to firmly engage a distal edge of the bore, allowing for precise measurement of the depth of the blind hole. It should be noted that the terms "proximal" and "distal" as used herein, refer to a direction toward (proximal) and away from (distal) a user of the device. The exemplary handle according to the invention aids in guiding the depth gauge into the bone while providing an easy to use interface permitting the individual movement of separate components of the depth gauge to allow for a precise measurement of the length of the blind hole. It should be noted that the terms "proximal" and "distal" as used herein, are intended to refer to a direction toward (proximal) and away from (distal) a user of the device.

As shown in FIGS. 1-4, a handle 200 according to an exemplary embodiment of the invention includes an elongated body 202 having a substantially rectangular cross-section, although other shapes may be used without deviating from the scope of the invention. The handle 200 includes first and second elongated channels 204, 206 extending longitudinally therethrough from a proximal end 208 to a distal end 210. In a first exemplary embodiment, a cross-sectional shapes of each of the first and second channels 204, 206 is substantially hexagonal, although other shapes may be used without deviating from the scope of the invention (e.g., circular, square, rectangular, etc.). An upper face 212 of the body 202 includes a first slot 214 formed therein open to a portion of the first channel 204 and a second slot 216 adjacent to the first slot 214 and open to the second channel 206. A first elongated shaft 218 slidably received within the first channel 204 includes a tab 220 extending from the first slot 214 by a length selected to permit ergonomic handling thereof by a physician or other user. It is noted that although the tab 220 is depicted as substantially cylindrical, any other shape may be employed without deviating from the scope of the invention. The first shaft 218 extends from a proximal end (not shown) to a distal end 222 having a housing 224 mounted thereon. In a preferred embodiment, the housing 224 is sold in a kit including the handle 200. As shown in greater detail in FIGS. 2-4, the housing 224 is offset relative to an axis of the first shaft 218 such that a channel 226 extending through the housing 224 is unobstructed by the first shaft 218. As will be described in greater detail later on, in use the channel 226 slidably receives first and second rods 102, 122 of a depth gauge 100. The handle 200 further comprises first and second pegs 234, 236 between the first and second slots 214, 216. Each of the pegs 234, 236 is substantially cylindrical and extends out of the upper face 212 by a distance selected to permit removable engagement thereof with corresponding portions of the depth gauge 100, as will be described in greater detail later on.

A second elongated shaft 228 slidably received within the second channel 206 includes a tab 230 extending out of the second slot 216 by a length selected to permit ergonomic handling thereof by a physician or other user. It is noted that although the tab 230 is depicted as substantially cylindrical, any other shape may be employed without deviating from the scope of the invention. A length of the second elongated shaft 228 is selected to prevent a distal end thereof (not shown) from extending distally out of the handle 200 regardless of the axial position of the tab 230. In another embodiment, the second channel 206 may be closed at a distal end thereof. The tab 230 includes a slotted opening 232 extending therethrough dimensioned to receive a leg 125 of the second rod 122 therethrough in an operative configuration, as will be described in greater detail later on.

The upper surface 212 of the handle 200 has a stepped shape and is further divided into first and second portions 213, 215 along lateral sides thereof. The first and second portions 213, 215 are separated along a central longitudinal axis 217 of the handle 200. A thickness of the second portion 215 is smaller than a thickness of the first portion 213 to accommodate the leg 125 of the second rod 122 of the depth gauge 100 therein, as will be described in greater detail with respect to the exemplary method below.

FIGS. 5-6 depict an exemplary single-use depth gauge 100 according to the invention. The depth gauge probe 100 is formed substantially similarly to the depth gauge disclosed in U.S. Provisional Appln. Ser. No. 61/582,025 entitled "Round Depth Gauge" filed on Dec. 30, 2012, the entire disclosure of which is incorporated herein by reference. The depth gauge 100 includes a first rod 102 extending from a proximal end 103 having an increased diameter portion 105. The increased diameter portion 105 is configured to removably engage the first and second pegs 234, 236 of the handle 200. Specifically, a groove 107 extends distally into the increased diameter portion 105 by a distance sufficient to permit insertion of the first peg 234 therethrough. The increased diameter portion 105 further comprises an opening 109 extending therethrough sized and positioned to slidably receive the second peg 236. The first rod 102 extends from the increased diameter portion 105 along an elongated shaft 106 to a distal end 108 from which an abutment 110 extends. The abutment 110 according to this embodiment has a triangular cross-section, although any other shape may be used without deviating from the scope of the invention. In an exemplary embodiment, a first proximal face 112 of the abutment 110 is substantially planar and extends substantially perpendicular to a longitudinal axis of the first rod 102. As those skilled in the art will understand, this configuration permits the proximal face 112 to be seated substantially flush against an opposing wall of a bone (not shown) in an operative configuration. That is, the proximal face 112 is angled to maximize a contacting surface area thereof with the bone, as will be described in greater detail with respect to the exemplary method below. The proximal face 112 has a substantially rectangular cross-section. The abutment 110 is positioned to protrude transversely away from the rod 102 in only one direction. As those skilled in the art will understand, this configuration permits a physician or other use to control an orientation of the abutment 110 relative to the housing 224. A width of the abutment 110 is selected to be smaller than a diameter of the channel 226 extending through the housing 224 but large enough so that, when the first rod 102 engages an insert 130 of a second rod 122, the abutment 110 extends radially beyond an outer edge of the housing 224. The width of the abutment 110 is also greater than a diameter of a cylindrical element 237 received at a proximal end of the depth gauge 100. Specifically, the element 237 is formed to receive proximal portions of the first and second rods 102, 122 therethrough. A diameter of the element 237 is smaller than a diameter of the housing 224 to permit insertion of the element 237 therethrough in an operative configuration. As those skilled in the art will understand, the element 237 maintains a spatial relationship of the first and second rods 102, 122 relative to one another.

Figure 2:
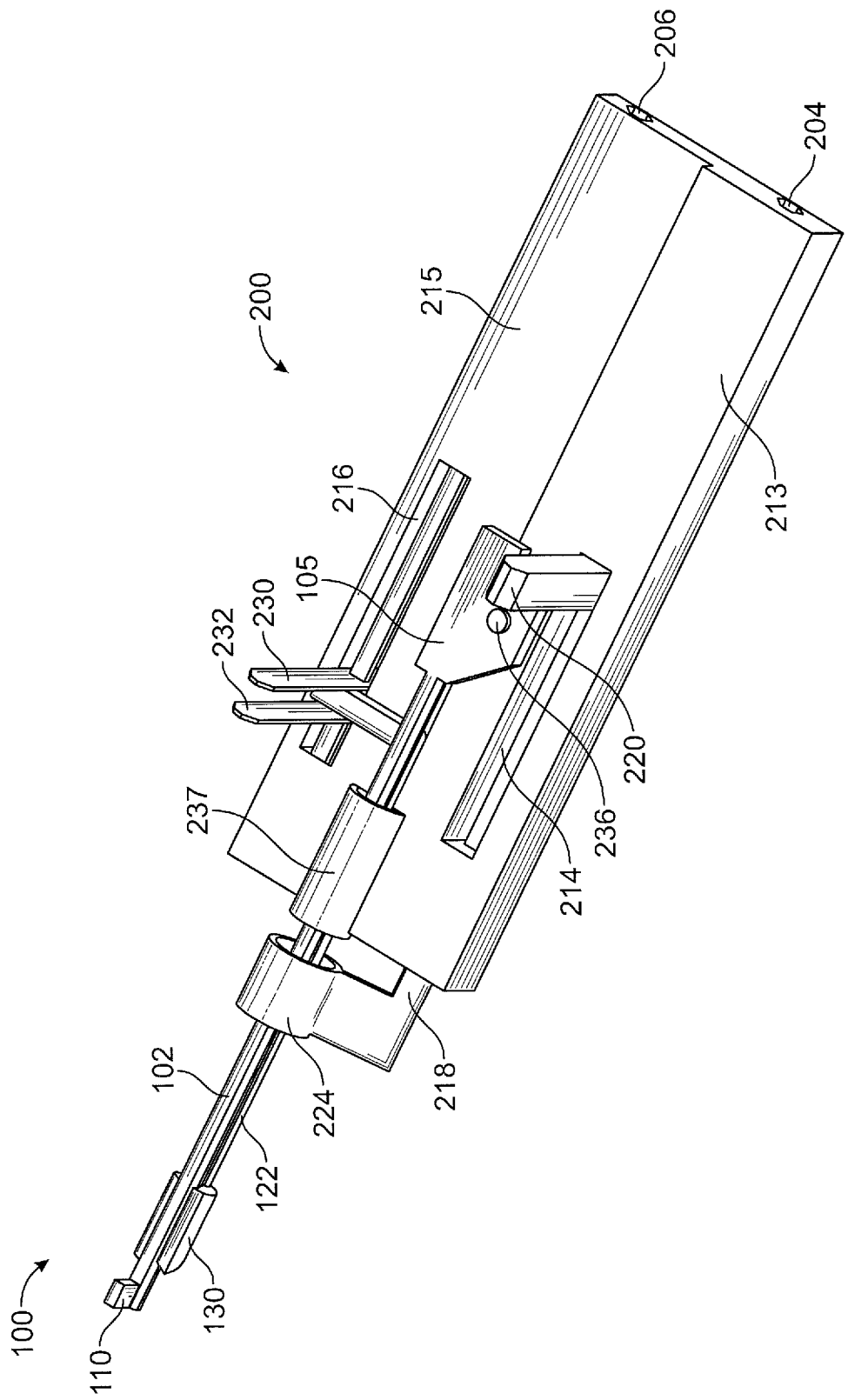
FIG. 2 shows a second perspective view of the depth gauge handle of FIG. 1.
Figure 3:
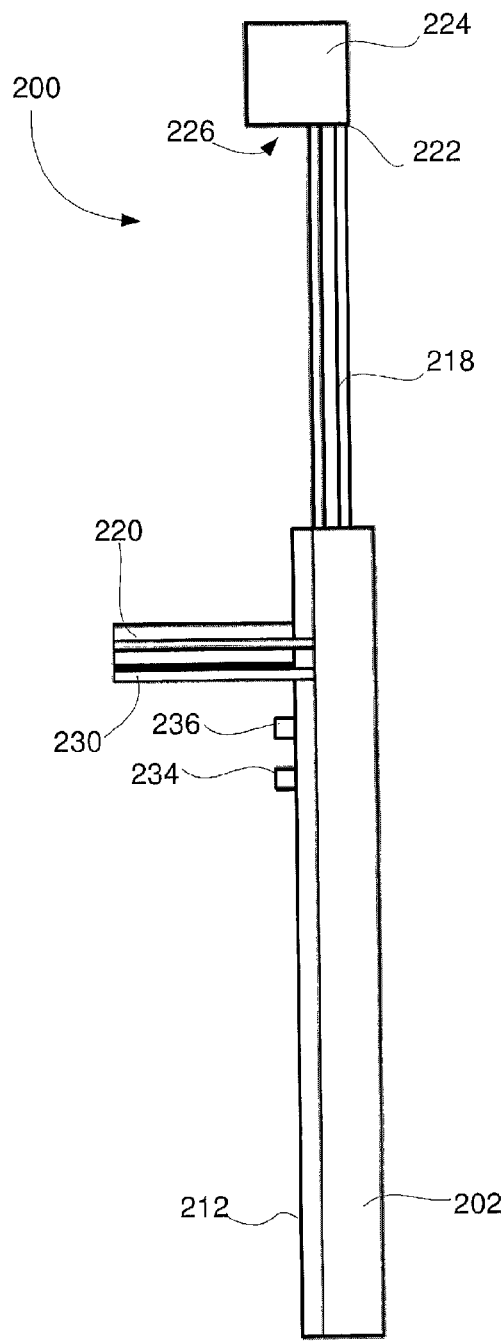
FIG. 3 shows a side view of the handle of FIG. 1 in a first operative configuration.
Figure 4:
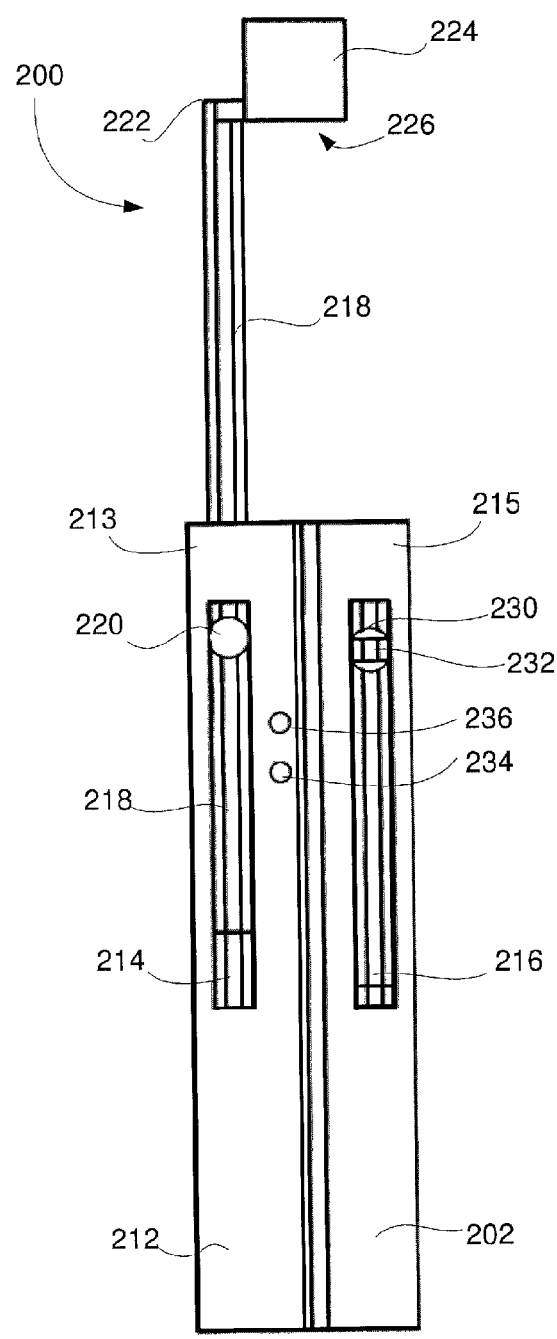
FIG. 4 shows a top view of the handle of FIG. 1 in the first operative configuration.

The second rod 122 extends from a proximal end 124 including a leg 125 and along an elongated shaft 126 to a distal end 128. The leg 125 of the second rod 122 extends substantially perpendicular to a longitudinal axis of the second rod 122 and has a width selected to permit slidable insertion of the leg 125 through the slotted opening 232 of the tab 230. The distal end 128 includes a substantially cylindrical insert 130 having a longitudinal axis which is offset from a longitudinal axis of the second rod 122. The insert 130 comprises a first opening 136 (shown in phantom) extending longitudinally therethrough, a cross-sectional shape of the first opening 136 being substantially cylindrical with a diameter selected to permit slidable insertion of the first rod 102 therethrough. As shown in FIGS. 1-2, the first opening 136 may be open to a side wall of the insert 130 to permit the first rod 102 to extend partially therefrom. The insert 130 further includes a second opening 138 permitting slidable insertion of the second rod 122 therethrough. A distal end of the insert 130 includes an angled wall 140 configured and dimensioned to guide insertion of the depth gauge 100 into a bone hole, as will be described in greater detail with respect to the exemplary method below.

In accordance with an exemplary method for the measurement of a bone hole according to the invention, the probe 100 is assembled with the first rod 102 received through the housing 224 within the opening 136 of the insert 130. The assembled first and second rods 102, 122 are received through the housing 224. The depth gauge 100 is positioned over the upper surface 212 of the handle 100 such that the first and second pegs 234, 236 are received within the groove 107 and opening 109 and the leg 125 is received through the slotted opening 232. In this configuration, the depth gauge 100 is locked to the handle 200. The handle body 202 is then manipulated to position the insert 130 against a proximal opening of a bone hole (not shown) drilled bicortically through a bone (not shown). The first rod 102 is then advanced distally through the bone hole until the abutment 110 extends distally out of the bone hole beyond a distal opening thereof. The tab 230 is then slid distally through the second slot 216 to move the distal end 128 of the second rod 122 distally through the bone hole engaging the angled wall 140 with walls of the bone hole which forces an axial alignment of the depth gauge 100 with a central longitudinal axis of the bone hole. The tab 230 is used to advance the second rod 122 distally relative to the first rod 102 until engagement of the proximal face 112 of the abutment 110 with the distal end 128 of the insert 130 prevents further distal movement of the second rod 122. Specifically, the size and cross-sectional shape of the proximal face 112 of the abutment 110 prevents it from being drawn into the substantially cylindrical opening 136 of the insert 130, as shown in FIG. 6. The first rod 102 is then retracted proximally until engagement of the proximal surface 112 of the abutment 110 with the distal opening of the bone hole 12 prevents further proximal retraction of the abutment 110. It is noted that during this step, a distally directed force is maintained on the second rod 122 to maintain the spatial relationship of the first and second rods relative to one another (i.e., with the proximal surface 112 of the abutment 110 in contact with the distal end 128 of the insert 130. This spatial relationship may be maintained through continued user pressure against the tab 230 or through any of a number of known mechanisms. For example, the tab 230 may frictionally engage the second slot 216 so that only a user-exerted force exceeding a predetermined minimum force permits movement of the tab 230. The combined diameter of the insert 130 and first rod 102 inserted therethrough is selected to be substantially equivalent to a diameter of the bone hole while the interaction between the first and second rods 102, 122 forces the abutment 110 to extend radially beyond an outer diameter of the bone hole preventing retraction of the abutment 110 proximally into the bone hole. In the next step, the tab 220 is advanced distally to move the housing 224 distally over the first and second rods 102, 122 until a distal end of the housing 224 contacts the proximal opening of the bone hole. A physician or other user may then accurately determine the depth of insertion of the depth gauge 100 and thus, the length of the bone hole based on a distance between a distal end of the housing 224 and the proximal surface 112 of the abutment 110. Specifically, the second rod 122 may be provided with markings (not shown) corresponding to a depth of insertion of the depth gauge 100 into the bone. In one non-limiting example, markings on the second rod 122 aligned with a proximal end of the housing 224 may indicate the length of the bone hole.

To remove the depth gauge 100 from the bone, the tab 230 is withdrawn proximally to permit retraction of the second rod 122, including the insert 130, out of the bone hole. As those skilled in the art will understand, the insert 130 may slide along the length of the shaft 106 until the insert 130 has been retracted from the bone hole. This retraction provides enough open space within the bone hole to permit the abutment 110 to be centered and moved through the bone hole. The handle 100 is then moved proximally to move the first rod 102 proximally out of the bone hole. Once the depth gauge 100 has been removed from the body, the depth gauge 100 may be slidably removed from the handle 200 and disposed of. The handle 200 may be then be sanitized according to a method known in the art and reused to perform any plurality of depth measurements.

It will be apparent to those skilled in the art that various modifications and variations can be made in the structure and the methodology of the present invention without departing from the spirit or scope of the invention. Thus, it is intended that the present invention cover the modifications and variations of this invention provided that they come within the scope of the appended claims and their equivalents.

What is claimed is:

1. A device for measuring blind holes formed through a bone, comprising:
   a depth gauge including a first elongated rod;
   a handle having an elongated body, an upper surface of the body having a peg extending therefrom to removably engage a proximal end of the first elongated rod of the depth gauge, the handle including a first slot extending into the upper surface and open to a first elongated channel extending through the handle;
   a first elongated shaft extending through the first elongated channel and including a first tab extending through the first slot, a range of movement of the first elongated shaft relative to the handle being limited by engagement of the first tab with walls of the first slot;
   a second slot extending into the upper surface of the handle and open to a second elongated channel extending through the handle; and
   a second elongated shaft extending through the second elongated channel and including a second tab extending through the second slot, a range of movement of the second elongated shaft relative to the handle being limited by engagement of the second tab with walls of the second slot wherein, in an operative configuration the second tab receives a proximal end of the depth gauge to control movement of an increased diameter insert at a distal end thereof.

2. The device of claim 1, wherein the second tab includes a slotted opening extending thereinto, the slotted opening receiving an extension leg provided at a proximal end of a second rod of the depth gauge, the extension leg extending at a transverse angle with respect to a longitudinal axis of the handle and depth gauge.

3. The device of claim 1, wherein the first tab frictionally engages the walls of the first slot.

4. The device of claim 1, wherein a distal end of the first elongated shaft is connected to a housing slidably receiving the first elongated rod and a second elongated rod of the depth gauge therethrough.

5. The device of claim 4, wherein a cross-sectional shape of the first and second elongated channels is substantially hexagonal.

6. The device of claim 4, wherein the housing is substantially cylindrical.

7. The device of claim 4, wherein a thickness of the handle at the second slot is smaller than a thickness of the handle at the first slot.

8. The device of claim 1, wherein a distal end of the second elongated channel is closed.

9. The device of claim 1, wherein the handle has a substantially rectangular cross-sectional shape.

10. A system for measuring blind holes formed through a bone, comprising:
a depth gauge including a first elongated rod and a second elongated rod, the first elongated rod including a shaft extending from a proximal end to a distal end, the distal end including an increased diameter abutment extending radially outward therefrom, the abutment including a proximal surface formed to contact a portion of the bone adjacent a distal opening of the blind hole to assume a locked configuration with the bone; and
a handle having an elongated body, an upper surface of the body having a first peg extending therefrom to removably engage a proximal end of the first elongated rod of the depth gauge, the handle including a first slot extending into the upper surface and open to a first elongated channel extending through the handle, the handle including a first elongated shaft extending through the first elongated channel and including a first tab extending through the first slot, a range of movement of the first elongated shaft relative to the handle being limited by engagement of the first tab with walls of the first slot, the handle also including a second slot extending into the upper surface and open to a second elongated channel extending through the handle, the handle including a second elongated shaft extending through the second elongated channel and including a second tab extending through the second slot, a range of movement of the second elongated shaft relative to the handle being limited by engagement of the second tab with walls of the second slot wherein, in an operative configuration the second tab receives a proximal end of the second elongated rod of the depth gauge to control movement of an increased diameter insert at a distal end thereof.

11. The system of claim 10, wherein the proximal end of the first elongated rod includes an increased diameter portion having a first substantially circular opening extending therethrough to engage the first peg formed on the handle.

12. The system of claim 11, wherein a proximal end of the increased diameter portion includes a second substantially circular opening open to a proximal end of the first elongated rod to engage a second peg formed on the handle.

13. The system of claim 10, wherein the insert formed on the distal end of the second elongated rod includes an opening extending therethrough to slidably receive the first elongated rod therethrough.

14. The system of claim 13, wherein a combined diameter of the insert and the first elongated rod received therethrough is one of substantially equivalent to and smaller than a diameter of the blind hole.

15. The system of claim 14, wherein engagement of the abutment with a distal end of the opening prevents the insert from moving distally relative to the abutment.

16. The system of claim 14, wherein a distal wall of the insert is angled to guide insertion thereof into the blind hole.

17. The system of claim 10, wherein the second tab is slotted to receive an extension leg provided at the proximal end of the second elongated rod of the depth gauge, the extension leg extending at a transverse angle with respect to a longitudinal axis of the handle and depth gauge.

18. The system of claim 10, wherein a distal end of the first elongated shaft is connected to a housing slidably receiving the first and second elongated rods of the depth gauge therethrough.

19. The system of claim 10, wherein a proximal end of the second elongated rod includes marking indicating a depth of insertion of the system into the blind hole.

20. A method for measuring a depth of a blind hole formed through a bone, comprising:
positioning a depth gauge over a guide handle such that a peg provided on the handle is received through a corresponding opening provided on a proximal end of the depth gauge, the depth gauge including a first elongated rod connected to the peg of the handle and a second elongated rod connected to a first tab of the handle;
positioning an insert of the second elongated rod of the depth gauge into a proximal opening leading into the blind hole and advancing the first elongated rod out of a distal opening of the blind hole such that an increased diameter abutment located at a distal end of the first elongated rod is positioned distally of the distal opening;
sliding the first tab of the handle distally to cause a corresponding distal movement of the second elongated rod relative to the first elongated rod such that a distal end thereof is positioned adjacent the abutment, a combined diameter of the abutment and the distal end of the second elongated rod being greater than a diameter of the distal opening;
retracting the handle to cause a corresponding retraction of the first rod until the abutment is seated against the distal opening; and
advancing a second tab of the handle distally, the second tab being connected to a housing encasing a proximal length of the first and second elongated rods therein, until a distal end of the housing contact the proximal opening so that the housing aligns with a marking corresponding to a depth of the blind hole.

21. The method of claim 20, wherein, when the insert is received within the blind hole, an axial position of the second elongated rod relative to the blind hole is maintained while retracting the first elongated rod proximally.

* * * * *